United States Patent
Dufour et al.

(10) Patent No.: US 9,645,126 B2
(45) Date of Patent: May 9, 2017

(54) SAMPLING METHOD FOR USE IN ODOR MEASUREMENT

(75) Inventors: Christian Dufour, Quebec (CA); Wissam Ezzedine, Longueuil (CA); Eric Debeuf, Montreal (CA); Eric Grossi, Grandcour (CH)

(73) Assignee: ODOTECH INC., Montreal (CA)

( * ) Notice: Subject to any disclaimer, the term of this patent is extended or adjusted under 35 U.S.C. 154(b) by 314 days.

(21) Appl. No.: 13/993,801

(22) PCT Filed: Dec. 19, 2011

(86) PCT No.: PCT/CA2011/001393
§ 371 (c)(1),
(2), (4) Date: Jun. 13, 2013

(87) PCT Pub. No.: WO2012/083432
PCT Pub. Date: Jun. 28, 2012

(65) Prior Publication Data
US 2013/0263644 A1    Oct. 10, 2013

Related U.S. Application Data

(60) Provisional application No. 61/424,760, filed on Dec. 20, 2010.

(51) Int. Cl.
*G01N 7/00* (2006.01)
*G01N 33/00* (2006.01)
*G01N 1/00* (2006.01)

(52) U.S. Cl.
CPC ..... *G01N 33/0016* (2013.01); *G01N 33/0022* (2013.01); *G01N 33/0031* (2013.01); *G01N 2001/002* (2013.01)

(58) Field of Classification Search
CPC .......... G01N 33/0009; G01N 33/0011; G01N 33/0031; G01N 33/0016
USPC ........................................... 73/23.2
See application file for complete search history.

(56) References Cited

U.S. PATENT DOCUMENTS

| 5,469,369 | A | * | 11/1995 | Rose-Pehrsson | .... G01N 29/022 340/632 |
| 6,494,077 | B2 | | 12/2002 | Aoyama et al. | |
| 7,802,485 | B2 | | 9/2010 | Wright et al. | |
| 8,481,470 | B2 | * | 7/2013 | Jones, Jr. | ............ G01N 1/2226 510/100 |

(Continued)

OTHER PUBLICATIONS

English Abstract of RU 2 327 984 C1, "Multi-Channel Piezo Sensor "Electronic Nose"", Published on Jun. 27, 2008.

*Primary Examiner* — Eric S McCall
*Assistant Examiner* — Mohammed E Keramet-Amircolai

(57) ABSTRACT

There are provided methods for detecting at least one odor in a gas sample. For example, such a method can comprise passing a gas sample into a thermal conditioning chamber or unit so as to control the temperature of the gas sample; dividing the gas sample into a plurality of portions and contacting each of the portions together with a different gas sensor. There is also provided an apparatus for detecting an odor that comprises a thermal conditioning unit adapted to control the temperature of a gas sample; a divider adapted to divide the gas sample into a plurality of gas portions; and a plurality of gas sensors disposed adjacently to the divider, each of the sensors being adapted to receive a portion of the gas sample in order to analyze it.

13 Claims, 1 Drawing Sheet

(56) References Cited

U.S. PATENT DOCUMENTS

| | | | | |
|---|---|---|---|---|
| 2002/0002857 | A1* | 1/2002 | Aoyama | G01N 1/24 73/23.34 |
| 2003/0003019 | A1* | 1/2003 | Raisanen | B08B 3/00 422/94 |
| 2004/0083793 | A1* | 5/2004 | Susko | G01N 21/7703 73/31.05 |
| 2005/0252275 | A1* | 11/2005 | Kita | G01N 33/0031 73/23.34 |
| 2006/0090542 | A1* | 5/2006 | Nakano | G01N 31/223 73/23.35 |
| 2009/0084198 | A1* | 4/2009 | Wright | G01N 1/2214 73/863.12 |
| 2011/0009986 | A1* | 1/2011 | Page | G01N 33/0031 700/90 |
| 2015/0000373 | A1* | 1/2015 | Hamidon | G01N 33/0001 73/23.34 |

* cited by examiner

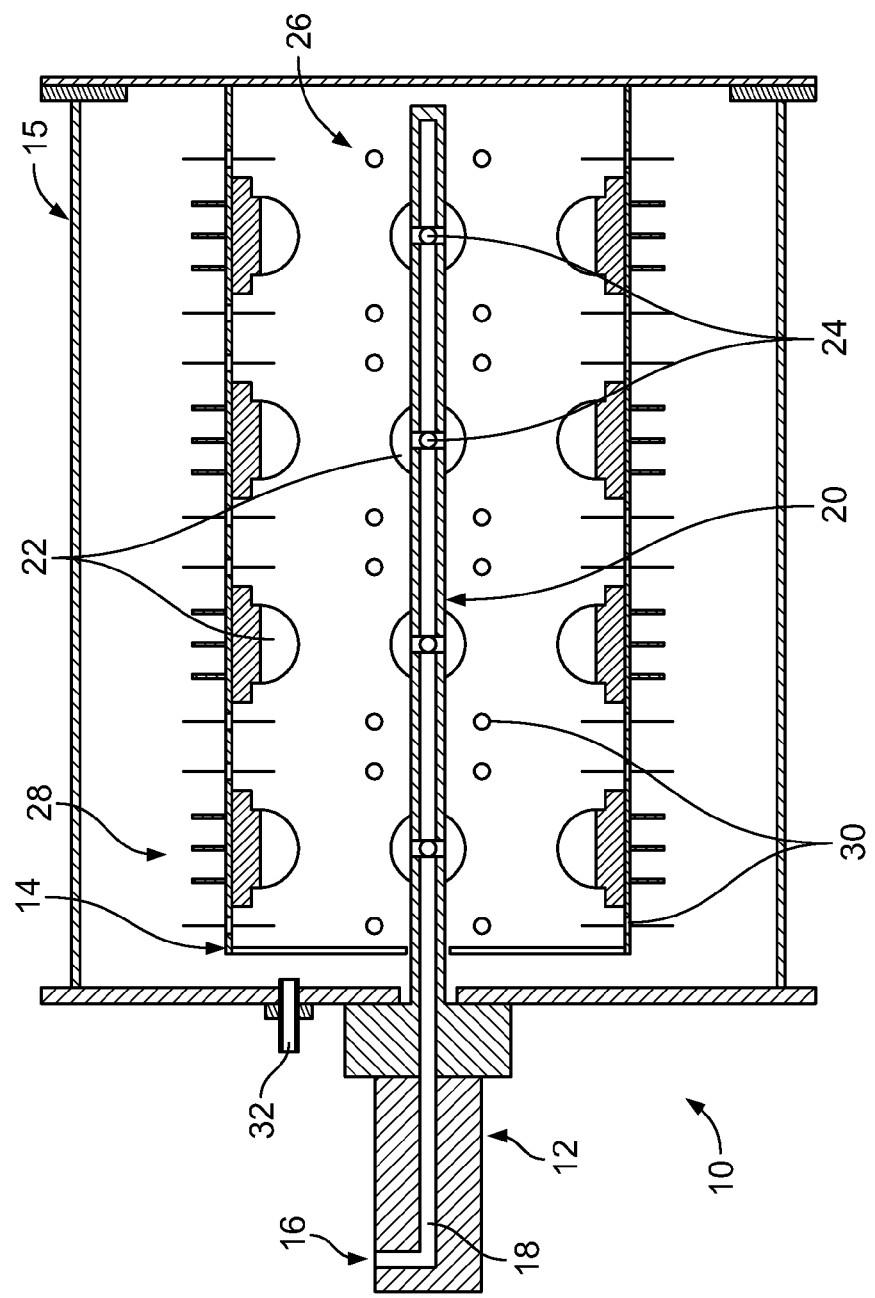

SAMPLING METHOD FOR USE IN ODOR MEASUREMENT

CROSS-REFERENCE TO RELATED APPLICATIONS

This application is a 35 USC 371 national stage entry of PCT/CA2011/001393 filed on Dec. 19, 2011 and which claims priority from U.S. provisional application No. 61/424,760 filed on Dec. 20, 2010. These documents are hereby incorporated by reference in their entirety.

FIELD OF THE DISCLOSURE

The present document relates to the field of odor detection and measurement. In particular, it relates to methods and apparatuses for detecting and/or measuring odors. It also relates to sampling methods for use in odor measurement.

BACKGROUND OF THE DISCLOSURE

Within the human genome, there is 1 gene for hearing, 3 genes for vision, 12 genes for tasting, and 1,000 genes for smelling. The human nose contains approximately fifty million neuro-receptors connected to ten thousand primary neurons. The latter are in contact with a second layer of neurons linked with the olfactory bulb in the cerebral cortex, which is where odors are recognized. In electronic noses, the neuro-receptors are replaced by a sensor matrix. The interactions between the different gas molecules and the sensors alter certain physical properties of the latter. The overall set of sensor matrix signals yields the "olfactory signature" or "odor pattern" characteristic of a given odor and odor concentration. In the case of the electronic noses, the two neuron layers and the cerebral cortex are replaced by an algorithmic odor recognition and quantification element. The network of artificial neurons is a common solution of this mathematical problem. It is the resemblance of the device with the human olfactory system that led to its being named an "electronic nose".

An odor is a quality of at least one chemical compound that stimulates the olfactory organ resulting in a sensation. Odor can be defined or quantified by various metrics such as the odor concentration, the odor intensity, the odor character, the odor persistence or the odor hedonic tone.

Odor concentration at the perception threshold is by definition 1 o.u./$m^3$ (odor unit per cubic meter). Odor concentration is expressed as multiples of the perception threshold. By definition [2], the odor unit is the quantity of odorous substance that, evaporated in 1 $m^3$ of odorless neutral gas (CNTP), triggers a physiological odor detection response in 50% of the population. The odor concentration of an odorous gas sample is determined by presenting that sample to a human panel, causing the concentration to vary due to dilution with a neutral gas in order to determine the dilution factor at the perception threshold of 50% of the panel. At that level of dilution the odor concentration, by definition, is 1 o.u./$m^3$. The EN 13725 standard enables, among other things, the determination of the concentration of an odor by means of dynamic olfactometry; since the samples presented to the panelists are not to undergo any pre-treatment, no method for drying the odorous air is used, and the dilution air itself is dry.

The passage from an olfactory signature (the set of sensor matrix responses to an odor of known composition and concentration) to the characterization (recognition and quantification) of the odor is affected by means of a mathematical model. After prior training, the mathematical model will thus correlate an odor (nature and concentration) with its olfactory signature. The mathematical model may take into account parameters other than the sensor responses; for instance, humidity, temperature, air flow or measurement chamber pressure.

There are today various electronic nose (or electronic sensor) technologies to meet the requirements of different industry sectors. The following are among the applications of electronic noses: quality control, environmental monitoring, research and development, the military and security sectors, and the health sector. Electronic noses make it possible to measure odors objectively, precisely, repeatably and continuously.

Different sensor technologies are used for electronic noses, such as MOS (Metal-Oxide Semiconductor), QMB (Quartz Microbalance), IRS (Infra-Red Sensor), CPS (Conducting Polymer Sensor), SAW (Surface Acoustic Wave), OFS (Optical Fiber Sensor), and others. These sensor types have different sensitivity, selectivity, robustness and service life characteristics. The choice and combination of technologies depends primarily on the type of application. Odorous molecule recognition and quantification is made indirectly by measuring changes in some physical properties of the sensors, such as electrical conductivity and the resonance frequency.

However, the sensors used into a sensor network for measuring odors have a limited measurement accuracy and a limited reproducibility of the signals obtained during measurement.

SUMMARY OF THE DISCLOSURE

According to one aspect there is provided a method of sampling a gaseous composition in an odor measurement method. The method comprises controlling the temperature of the gaseous composition so as to obtain a desired temperature; and dividing the gaseous composition into a plurality samples having substantially the same volume and substantially the same constituents and measuring each of the samples with a different sensor adapted for measuring odors.

A method for detecting at least one odor in a gas sample, the method comprising:
 passing a gas sample into a thermal conditioning chamber or unit so as to control the temperature of the gas sample; and
 dividing the gas sample into a plurality of portions and contacting each of the portions with a different gas sensor.

According to another aspect there is provided a method for detecting at least one odor in a gas sample, the method comprising:
 controlling the temperature of a gas sample so as to obtain a desired temperature;
 dividing the gas sample into a plurality of gas jets; and
 contacting together the plurality of gas jets with a plurality of sensors.

According to another aspect there is provided an apparatus for detecting an odor, the apparatus comprising
 a thermal conditioning unit adapted to control the temperature of a gas sample;
 a divider adapted to divide the gas sample into a plurality of gas portions, the divider being in fluid flow communication with the thermal conditioning unit;
 a plurality of gas sensors disposed adjacently to the divider and in fluid flow communication with the divider, each of the sensors being adapted to receive a portion of the gas sample in order to analyze it.

BRIEF DESCRIPTION OF THE DRAWINGS

Further features and advantages will become more readily apparent from the following description of various embodiments as illustrated by way of examples in the appended drawings wherein:

The FIGURE is a cross-section schematic representation of an apparatus for detecting and measuring odors according to an example of the present disclosure.

DETAILED DESCRIPTION OF VARIOUS EMBODIMENTS

The following examples represent in a non-limitative manner, various specific embodiments.

As in can be seen in The FIGURE, there is provided an apparatus 10 for detecting and measuring odors. The apparatus comprises a thermal conditioning unit (or chamber) (12) and a measuring chamber (14). The apparatus (10) is also provided with a housing (15) and a measured gas chamber (28) that is defined between the measuring chamber (14) and the housing (15). The thermal conditioning unit comprises an inlet (16) in fluid flow communication and a main conduit (18), the latter being in fluid flow communication with the measuring chamber (14). The thermal conditioning unit (12) can be adapted to heat or cool down the temperature of the entering flow of gas. The measuring chamber (14) comprises a main conduit (20) (manifold or dispatching tube) that is in fluid flow communication with the main conduit (18) of the thermal conditioning unit (12). The two conduits (18 and 20) can be the same or different. The measuring chamber (14) also comprises a plurality of sensors (22). The main conduit (20) is provided with a plurality of outlets (24). Each outlet (24) being disposed adjacently to a sensor (22) and adapted to direct a jet of gas on the sensor (22). Each of the sensors (22) being disposed in an isolation cell (26) and is thus independent from the other sensors. By using such a configuration, the samples of gas contacting the sensors (22) in the form of a jet will all be substantially the same in terms of their properties (temperature, concentration of various components etc.). Thus, the sensors (22), even if they are close or remote from the thermal conditioning unit (12), will be submitted to substantially the same gas sample.

In order to supply each sensor (22) with a gas sample not corrupted, substantially identical in physical manner and qualitative manner, the main stream sample was passed through the thermal conditioning unit (12) directly which was coupled to the measuring chamber (14) to eliminate any thermal alteration. The sampling gas is then distributed (fractionated) through the conduit (20) dividing the gas sample into equal parts on each of the sensors (22). The gas flows radially from the main conduit (20) through outlets (24) radially extending from the main conduit (20). The gas thus flows from inside the main conduit (20) of the measurement chamber (14), through the radially extending outlets (24) (fractionation) and then to outside to hit the measurement surface of sensors (22). The gas is then redirected into the measured gas chamber (28) through openings (gas draining holes (30)) contiguous to the sensors (22). The gas is then conveyed outside of the (28) by means of an outlet (32).

It was found that by isolating the sensors (22) from one another, it was possible to substantially avoid the interferences caused by an uncontrolled thermal convection. The electronic circuits control of the sensors (22) forming the measuring cells (26) were equipped with a heating transistor (not shown) disposed outside of the cells and into the gas collector (not shown), thereby allowing for a constant thermal radiation on each measuring elements or sensors (22).

Every sensor (22) had its own operating temperature controller to provide the maximum sensitivity on the output signal. Such a configuration ensures an efficient way to provide a specific operating environment and also isolate each sensor (22) of them from their interferences.

In the above-mentioned methods and apparatuses, the portions can be equivalents in terms of quantity of gas and/or in terms of their constituents.

For example, the gas sample can be divided into a plurality of gas jets or streams that are each directed towards a sensor so as to contact the sensor.

For example, each of the jets can be in contact with a different sensor.

For example, the gas jets can have a diameter that is equal or inferior to a diameter of the sensors.

For example, the gas jets can have a diameter that is about 1.5, about 2 or about 3 times inferior to a diameter of the sensors. For example, the gas jets can have a diameter that is about 1.5 to about 3 times inferior to a diameter of the sensors.

For example, the gas jets can have a diameter that is about 2 to about 10 times inferior to a diameter of the sensors.

For example, the gas jets can have a diameter that is about 2 to about 20 times inferior to a diameter of the sensors.

For example, the gas sample can be passed through a manifold comprising a plurality of outlets radially and outwardly extending therefrom, each of the outlet can be disposed in an isolated cell comprising a gas sensor adapted to be contacted by a gas jet exiting from the outlet.

For example, the gas sensors can be disposed in independent cells.

For example, the divider can be adapted to divide the gas sample into a plurality of gas jets.

By using the above-mentioned method and apparatus for sampling gases in odor measurement, it was found that contrarily to the prior art solutions known to the inventors of the present application, the sensors used in the present technology were not influenced by the temperature variation of the gas samples submitted. By using the technology described in the present application, thermal interferences between each of the sensors has been substantially avoided. The chemical composition of the samples was not altered along the flow line after a catalytic decomposition resulting from the reaction of the MOS surfaces, which was the case with the prior art solutions known to the inventors. Thus, by using the method and apparatus described in the present disclosure, it was possible to obtain odor measurements with a greater reproducibility of the signals obtained during measurement and also a greater accuracy of the measurements.

While a description was made with particular reference to the illustrated embodiments, it will be understood that numerous modifications thereto will appear to those skilled in the art. Accordingly, the above description and accompanying drawings should be taken as specific examples and not in a limiting sense.

What is claimed is:

1. A method for detecting at least one odor in a gas sample, said method comprising:

passing a gas sample into a thermal conditioning chamber or unit so as to control the temperature of said gas sample;

dividing the temperature controlled gas sample into a plurality of portions, wherein said portions are equivalents in terms of quantity of gas and/or in terms of their constituents; and contacting each of said portions together with a different gas sensor, wherein said sensors are isolated from one another, thereby substantially avoiding an interference caused by an uncontrolled thermal convection.

2. The method of claim 1, wherein the temperature controlled gas sample is divided into a plurality of gas jets or streams that are each directed towards a sensor so as to contact said sensor.

3. A method for detecting at least one odor in a gas sample, said method comprising:

controlling the temperature of a gas sample so as to obtain a desired temperature;

dividing said gas sample having said desired temperature into a plurality of gas jets, wherein said gas jets are equivalents in terms of quantity of gas and/or in terms of their constituents; and contacting together said plurality of gas jets with a plurality of sensors for measuring and/or detecting odors.

4. The method of claim 3, wherein each of said jets is in contact with a different sensor.

5. The method of claim 3, wherein said gas jets have a diameter that is equal or inferior to a diameter of said sensors.

6. The method of claim 4, wherein said gas jets have a diameter that is about 1.5 to about 3 times inferior to a diameter of said sensors.

7. The method of claim 4, wherein said gas jets have a diameter that is about 2 to about 10 times inferior to a diameter of said sensors.

8. The method of claim 4, wherein said gas jets have a diameter that is about 2 to about 20 times inferior to a diameter of said sensors.

9. The method of claim 4, wherein said sample is passed through a manifold comprising a plurality of outlets radially and outwardly extending therefrom, each of said outlets being disposed in an isolated cell comprising a gas sensor adapted to be contacted by a gas jet exiting from said outlet.

10. A method of sampling a gaseous composition in an odor measurement method, said method comprising controlling the temperature of said gaseous composition so as to obtain a desired temperature; dividing said gaseous composition having said desired temperature into a plurality of samples having substantially the same volume and substantially the same constituents; and measuring each of said samples with a different sensor adapted for measuring odors.

11. An apparatus for detecting an odor, said apparatus comprising a thermal conditioning unit adapted to control the temperature of a gas sample;

a divider adapted to divide said temperature controlled gas sample into a plurality of gas portions, said divider being in fluid flow communication with said thermal conditioning unit, and wherein said portions are equivalents in terms of quantity of gas and/or in terms of their constituents; and a plurality of gas sensors that are isolated from one another, said gas sensors being disposed adjacently to said divider and in fluid flow communication with said divider, each of said sensors being adapted to receive a portion of said temperature controlled gas sample in order to analyze it, thereby substantially avoiding an interference caused by an uncontrolled thermal convection.

12. The apparatus of claim 11, wherein said gas sensors are disposed in independent cells.

13. The apparatus of claim 12, wherein said divider is adapted to divide said gas sample into a plurality of gas jets.

* * * * *